United States Patent [19]

Wagenknecht, deceased et al.

[11] 4,150,112

[45] Apr. 17, 1979

[54] PLAQUE INHIBITING COMPOSITION AND METHOD

[75] Inventors: Austin C. Wagenknecht, deceased, late of Hennepin County, Minn., by Don Austin Wagenknecht, personal representative; George V. Daravingas, Edina; William E. Koski, Minneapolis, both of Minn.

[73] Assignee: General Mills, Inc., Minneapolis, Minn.

[21] Appl. No.: 855,537

[22] Filed: Nov. 28, 1977

[51] Int. Cl.² ............................................. A61K 9/68
[52] U.S. Cl. ...................................... 424/48; 424/49; 424/56; 424/58
[58] Field of Search ..................... 424/48–58; 426/3–6

[56] References Cited

U.S. PATENT DOCUMENTS

| | | | |
|---|---|---|---|
| 2,366,589 | 1/1945 | Borglin | 426/3 X |
| 2,744,049 | 1/1956 | Salzmann | 424/49 X |
| 3,655,866 | 4/1972 | Bilotti | 424/48 |
| 3,818,107 | 6/1974 | Yolles | 426/3 |
| 3,821,417 | 6/1974 | Westall et al. | 426/3 |
| 3,899,593 | 8/1975 | Hammond et al. | 426/3 |
| 3,914,434 | 10/1975 | Bohni | 424/343 |
| 3,930,026 | 12/1975 | Clark | 426/3 |
| 3,973,041 | 8/1976 | Du Ross | 426/3 |
| 4,000,320 | 12/1976 | Klose et al. | 426/3 |
| 4,022,880 | 5/1977 | Vinson et al. | 424/49 |

FOREIGN PATENT DOCUMENTS

| | | |
|---|---|---|
| 959764 | 12/1974 | Canada. |
| 1290627 | 9/1972 | United Kingdom. |
| 1296952 | 11/1972 | United Kingdom. |
| 1372932 | 11/1974 | United Kingdom. |

*Primary Examiner*—Shep K. Rose
*Attorney, Agent, or Firm*—Gene O. Enockson; John A. O'Toole

[57] ABSTRACT

This invention discloses compositions effective in inhibiting or reducing plaque in the oral cavity. Chewing gums are a preferred vehicle for delivering the plaque inhibiting benefit of the present invention.

13 Claims, No Drawings

PLAQUE INHIBITING COMPOSITION AND METHOD

BACKGROUND OF THE INVENTION

1. Field of the Invention

This invention relates to the practice of dental hygiene, and in particular, to the removal of, or the inhibition of the growth of plaque in the oral cavity.

2. Description of the Art

The following references, while not exhaustive discuss various materials which are included in compositions which contact the oral cavity. Salzmann, in U.S. Pat. No. 2,744,049 issued May 1, 1956, discusses dental creams containing a partial ester of glycerine and a higher fatty acid material. The Salzmann patent also discusses the use of dicalcium phosphate dihydrate as an abrasive, and as well the use of sodium lauryl sulfate. U.S. Pat. No. 3,622,662 issued to Roberts et al, Nov. 23, 1971, describes dental creams which may contain various zinc salts or sodium lauryl sulfate and compositions which may be flavored with peppermint, spearmint or clove oils.

Clark, in U.S. Pat. No. 3,930,026 issued Dec. 30, 1975, describes the enhancement of flavor in chewing gums obtained by sorbing the flavoring onto a hydrophilic colloid in conjunction with a surfactant. Among the surfactants disclosed are anionic materials, including sodium di(2-ethylhexyl)sulfosuccinate. Clark also states that nonionic surfactants may be used to sorb the flavor into the gum including fatty acid monoglycerides or fatty acid diglycerides. British Pat. No. 1,290,627 in the name of Pader, published Sept. 27, 1972, describes mouthwashes, having activity against calculus and plaque, containing zinc salts and further describing the use of sodium lauryl sulfate to provide foaming action.

British Pat. No. 1,296,952 reported by Cancro et al and published Nov. 22, 1972, states that plaque and calculus may be diminished by zinc phenolsulphonate and certain enzymes in dentifrice compositions. The Cancro patent also describes the use of certain abrasives, buffering agents, and various surfactants. British Pat. No. 1,372,932 published Nov. 6, 1974, describes purported anticaries compositions including chewing gums, dentifrices and candylike products. In particular, the aforementioned British patent states that stearoyl-2-lactylate has been found effective to inhibit the production of dextran in the mouth.

Canadian Pat. No. 959,764 issued Dec. 24, 1974, to Pader, describes dentifrice compositions containing a source of zinc ions and various enzymes. Pader also describes various surfactants which may be included in toothpastes, including sodium lauryl sulfate and dioctyl sodium sulfosuccinate.

U.S. Pat. No. 4,022,880 issued to Vinson et al, on May 10, 1977, describes compositions for inhibiting dental plaque containing a source of zinc ions and a halosalicylanilide, a quaternary ammonium compound and other specified materials. The Vinson et al patent also states that sodium lauryl sulfate and polishing agents may be used in the compositions. Hass in Ser. No. 124,465, filed Mar. 15, 1971 discloses that stearoyl-2-lactylate may be used to prevent the formation of dextran in the mouth.

Yolles, in U.S. Pat. No. 3,818,107 issued June 18, 1974, describes chewing gums which incorporate the flavor in a polymeric backbone. Yolles states that the flavor release in the chewing gum is sustained by the molecular arrangement of the flavor group. In U.S. Pat. No. 3,651,206 issued to Litchfield et al on Mar. 21, 1972, are described chewing gums containing various aliphatic aldehydes as anticaries agents. Various oral preparations for preventing dental plaque are described in U.S. Pat. No. 3,940,476 issued Feb. 24, 1976 to Hass. Comollo states in U.S. Pat. No. 3,984,574 issued Oct. 5, 1976 that non-tacky chewing gums may be made containing mono- and diglycerides of fatty acids in an amount up to ten percent (10%) by weight of the base composition.

U.S. Pat. No. 3,821,417 issued to Westall et al on June 28, 1974, describes the use of dihydrochalcone in chewing gums. This patent further describes the use of butylated hydroxyanisole, butylated hydroxytoluene and propyl gallate as antioxidants in chewing gums. DuRoss, in U.S. Pat. No. 3,973,041 issued Aug. 3, 1976 describes the use of sorbitol powder, butylated hydroxyanisole, and glycerine in chewing gums. Additional disclosures of sorbitol as well as other sugars, such as xylitol, are made in various U.S. patents including: U.S. Pat. No. 4,000,320 issued to Klose et al on Dec. 28, 1976; U.S. Pat. No. 3,899,593 issued to Hammond et al on Aug. 12, 1975; U.S. Pat. No. 3,914,434 issued Oct. 21, 1975 to Bohni; U.S. Pat. No. 3,296,079 issued Jan. 3, 1967 to Griffin; and U.S. Pat. No. 3,655,866 issued Apr. 11, 1972 to Billoti.

Dental plaque is a deposit which accumulates on the teeth and adjacent surfaces in the oral cavity. The plaque is a product of microbial growth, primarily derived from food residues in the mouth. Mucoproteins and minerals present from the saliva and dead cells in the mouth also assist in plaque formation.

Plaque is removed to some extent by effective brushing of the teeth, but the less accessible and more sheltered areas of the mouth which cannot be readily reached by a toothbrush, are particularly susceptible to plaque and eventually, calculus growth. Left unhindered, the plaque increases in size and more tenaciously adheres to the teeth. The bacterial metabolism within the plaque on the tooth surface results in the production of acids, toxins and enzymes which are deleterious to the neighboring oral tissues. It has been stated that there is evidence pointing to plaque as being the direct cause of dental caries, due to the generation of acids within the plaque structure. In any event plaque is unsightly, and undesirable.

The present invention describes ingredients in compositions to retard and/or remove plaque from the surface of the teeth. It is also noted that when the plaque is removed or prevented from forming upon the teeth, that the potential growth of calculus is also advantageously limited.

The embodiments of the plaque inhibiting composition are described below in the summary of the invention.

Throughout the specification and claims, percentages and ratios are by weight, and temperatures are in degrees Celsius, unless otherwise indicated.

SUMMARY OF THE INVENTION

The present invention encompasses a food product to moderate the incidence of dental plaque containing an effective amount of:

(a) an alkyl sulfate salt; and, (b) a member selected from the group consisting of zinc compounds and a plaque inhibiting flavor selected from the group consisting of cinnamon oil, peppermint oil, and spearmint oil, and mixtures thereof in a weight ratio of from about 1,000:1 to about 1:1,000.

The present invention also includes a chewing gum comprising:

(a) from about 10% to about 95% by weight of a gum base; and, (b) from about 0.001% to about 20% by weight of a mixture of an alkyl sulfate salt and a member selected from the group consisting of zinc compounds and a plaque inhibiting flavor selected from the group consisting of cinnamon oil, peppermint oil, and spearmint oil and mixtures thereof in a weight ratio of from about 1,000:1 to about 1:1,000.

DETAILED DESCRIPTION OF THE INVENTION

As is shown in the summary of the invention, the plaque inhibiting compositions of the present invention may take several forms. That is, the present invention is concerned with the application of the compositions described herein to the oral cavity as either solid form food products or as a chewing gum.

In the food product line, the present invention envisages all forms of solid foods such as cocoa powders, potato chips, cheese curls, candies in both hard and soft forms including chocolates, mints, troches, lozenges, chewable stick candy, and the like. Of particular interest in the present invention are all forms of chewing gum which provide an excellent delivery system for the compositions of the present invention.

Chewing gums include those with natural and synthetic bases as described below and are also inclusive of bubble gum. Chewing gum is the preferred vehicle for delivering the compositions of the present invention because, due to the inherent nature of chewing gum, a prolonged contact with the oral cavity is reached. Moreover, the gum base can provide sustained release of the active components of the present invention, thus minimizing the amount of the active compounds that must be used.

As used in the present invention the term effective amount of the composition is used synonymously with the term sufficient amount, both terms referring to the amount of the composition required to achieve plaque reduction or inhibition. There is no set definition for the amount of the composition required to achieve the desired plaque inhibition. That is, the formulation of the food product or the chewing gum will be set such that in ordinary use a sufficient amount of the active components will be delivered to achieve the anti-plaque benefit.

The alkyl sulfate salt utilized to moderate the incidence of dental plaque in the present invention, is commonly used in detergent compositions. In as much as this component is well-known, no detailed discussion of the manufacture of the alkyl sulfate salt is given herein. The amount of the alkyl sulfate salt in the various forms of the present invention, is generally within the range of 0.001% to about 15% by weight thereof. In its preferred applications, the alkyl sulfate salt is used at from about 0.005% to about 5%, preferably from about 0.01% to about 3% by weight of the composition.

The term alkyl as used above includes those salts having from about 10 to about 18 carbon atoms. Preferably the alkyl sulfate salt is based upon the corresponding even numbered alcohol. Most preferably the alkyl sulfate salt is lauryl sulfate.

The zinc compound is utilized to supply a source of zinc ions to the oral cavity. The zinc compound as previously stated, is utilized at a level of from about 0.001% to about 5%, preferably from about 0.005% to about 3%, and most preferably from about 0.01% to about 2% by weight.

The foregoing amounts of the zinc compound are sufficient to provide a level of about 50 parts per million of zinc ion. Preferably, the composition is formulated such that greater than 75 parts per million and most preferably greater than 130 parts per million of the zinc ion is available from the composition.

The zinc compound is not limited to any one source of zinc ions. For instance, suitable salts which supply zinc ions include the phosphates, sulfates, chlorides, fluorides, oxides and zinc fatty acids. Of particular interest are zinc phenolsulfonate, zinc oxide and the stearic acid salt of zinc. The last mentioned component is particularly useful in that it also serves a lubricant function which is desirable when forming tablets such as for the mint or hard candy variation of the present invention.

In the present invention, the weight ratio of the alkyl sulfate salt to the zinc compound should be in the range of from about 1,000:1 to about 1:1,000, preferably from about 250:1 to about 1:250 and most preferably from about 20:1 to about 1:20.

The plaque inhibiting flavors of the present invention are the essential oils selected from the group consisting of cinnamon oil, peppermint oil, and spearmint oil, as well as mixtures thereof. The use and preparation of the various essential oils which have been found to inhibit plaque formation in the compositions of the present invention are well known and widely used in the food industry. In as much as these essential oils have been widely approved and used, benefits to the present invention are thus two fold. First, these essential oils may be used to flavor the compositions, such as the preferred chewing gum aspect of the present invention, and second these materials, which are generally regarded as safe, have the ability to inhibit plaque formation.

The first of the essential oils discussed is cinnamon oil. Cinnamon oil consists largely of two primary ingredients, namely cinnamic aldehyde (also known as cinnamal) and eugenol. Both of the aforementioned components exist naturally in cinnamon oil in varying concentrations determined by the particular source from which the cinnamon oil is derived. Specifically Ceylon Cinnamon Bark contains the cinnamic aldehyde at from about 50% to 90% by weight of the steam distillate of the bark. The eugenol content will ordinarily vary in distillate at from about 2% to 15% by weight.

In addition to obtaining the bark distillate from the Ceylon cinnamon tree, the bark distillate of Saigon cinnamon has a similar composition. The Saigon cinnamon is found in the Saigon district of Vietnam and is reputed to have peculiar odor and flavor to that of all other forms of cinnamon bark distillate. Other suitable sources of the cinnamon bark distillate include Chinese cinnamon which grows wild in Southeast Asia.

In addition to using the distillate of the dried inner bark of the shoots of the coppiced trees; the leaves of the Ceylon, Saigon and Chinese cinnamon trees may also be used as a source of cinnamon oil.

The leaves of the various cinnamon trees have a reverse content of the eugenol and cinnamic aldehyde. Typically, the eugenol content runs from 70% to 98% by weight of the leaf oil, while the cinnamic aldehyde is generally from about 1% to 10% by weight of the leaf oil.

Various other components also make up a minor portion of cinnamon bark or cinnamon leaf oil. These components include caryophyllene, beta-phellandrene, p-cymene, 1-alphapinene, 1-linalool, furfural, cinnamic alcohol, benzyl benzoate, cinnamyl acetate, benzaldehyde, methyl salicylate, salicylaldehyde, and coumarin.

Cinnamon oil is the preferred plaque inhibiting flavor in the present invention. The use of the term cinnamon oil is meant to embrace a member of the group consisting of cinnamon aldehyde and eugenol as well as mixtures thereof. A particularly interesting method of including cinnamon aldehyde in the composition of the present invention is found in U.S. Pat. No. 3,818,107 issued to Yolles, on June 18, 1974, herein incorporated by reference. The Yolles patent basically states that a sustained release of flavor may be obtained by incorporating the cinnamon aldehyde into a polymer backbone. The sustained release is apparently obtained by the hydrolyzing effect of the saliva upon the polymer backbone which then releases the cinnamon aldehyde to give continuous release of the flavor. In the present invention, of course, not only is the continuous flavor achieved but also a sustained release of one of the plaque inhibiting ingredients of the present composition.

The next plaque inhibiting flavor to be discussed in spearmint oil. Spearmint oil is obtained by the steam distillation of the flowering tops of Mentha spicata Houds or L. Labiatae. The spearmint oil contains alpha-pinene, alphaphellandrene, 1-limonene, octyl alcohol, dihydrocarveol, carvone, and in some varieties dipentene cineol. Of the aforementioned components the carvone is the active material in the essential oil and will ordinarily be found at a concentration of from about 40% to 90% by weight of the spearmint oil.

The last of the plaque inhibiting flavor oils to be discussed is peppermint. Peppermint oil is derived from plants in the Labiatae family and in particular from Mentha piperita L. As with the other plaque inhibiting flavors, peppermint oil is obtained by steam distillation of the flowering plant in yields ranging from about 0.3% to 0.7% depending upon the particular origin of the plant.

The main constituents found in peppermint oil include menthone, isomenthone menthofuran, menthol, neomenthol, isomenthol menthyl acetate, and piperitone. Of the foregoing components menthol in its free or esterified state is the active component and is found in the oil at levels from about 40% to 70% by weight of which approximately 80% is in free form and 20% as esterified menthol.

Further information on the composition of the plaque inhibiting flavors of the present invention may be obtained from Fenaroli's Handbook of Flavor Ingredients, Second Edition, Volumes 1 and 2, 1975; published by CRC Press, Inc., of Cleveland, Ohio. As it was previously noted, the various plaque inhibiting flavors may be used in mixtures with one another as well as separately to obtain the benefits of the present invention. It is also noted that very interesting flavor combinations arise when using mixtures of the various essential oils.

The plaque inhibiting flavors of the present invention are generally utilized at a level of about 0.05% to about 10%, preferably from about 0.08% to about 5%, and most preferably at about 0.1% to about 3% by weight of the composition. While the discussion given above is concerned primarily with natural sources of the plaque inhibiting flavor oils, it is to be noted that the benefits may be obtained from essential oils containing various synthetic components.

The present invention is particularly concerned with the use of chewing gums as a means for delivering anti-plaque compositions. First, chewing gums are ordinarily used such that prolonged contact with the surface of the teeth and gums is obtained. Secondly, the mastication or chewing of the gum aids in cleaning or hindering the ability of plaque to tightly adhere to the teeth. In chewing gums, a gum base is a necessary component.

All manner of natural or synthetic gum bases are to be considered as included within the scope of the present invention. Examples of suitable gum bases include chicle, gutta percha, jelutong, balata, namaquland rubber, almeidana gum, abba rubber, gutta siak, gutta cotie, gutta kay, gutta hangkang, gutta jangkar, gutta sundik, gutta soh, gutta susu, gutta penang, and yellow gutta. Further examples of gum bases include rosins, such as cumarone resin, pontianak resin, copal gum, kauri gum, dammar gum, sweet bay gum, spruce gum, and balsams. Moreover, suitable gum bases include crown gum, nispero, rosidinha, pendare, perillo, niger gutta, and tuno.

Additional chewing gum base materials include elastimers such as polyisobutylene, polyisoprene, isobutyleneisoprene copolymers and copolymers of butadiene and styrene, hydrogenated or partially hydrogenated vegetable oils such as soy bean, cotton seed, corn, peanut, and palm or animal fats such as tallow and lard. In addition paraffin, beeswax, petroleum wax, polyethylenes, and polyvinylacetates may be employed. Further descriptions of suitable chewing gum bases are found in U.S. Pat. No. 2,366,589 issued to Borglin Jan. 2, 1945; U.S. Pat. No. 3,821,417, issued to Westall, et al on June 28, 1974; U.S. Pat. No. 4,041,179 issued to Stubits et al on Aug. 9, 1977; and U.S. Pat. No. 3,984,574 issued to Comollo on Oct. 5, 1976; all of which are herein incorporated by reference.

The amount of the gum base utilized in the chewing gum aspect of the present invention is from about 10% to about 95%, preferably from about 15% to about 70% by weight of the chewing gum composition.

While no sweetener is required in the present invention, it is desired that the product be appetizing to consumers. Thus, any form of natural or synthetic sweetener may be included in the present invention. It is preferred, however, that sucrose, fructose, and glucose content of the compositions be restricted or eliminated due to the fact that these materials provide "food" from which plaque may be formed. Artificial sweeteners such as saccharin, cyclamates, and dihydrochalcones may be included at conventional amounts in the compositions of the present invention.

A preferred source of sweetening agents for the present invention are members selected from the group consisting of xylitol, sorbitol, and mannitol as well as mixtures thereof. The foregoing polyol sugars are generally utilized at from about 5% to about 80%, preferably from about 10% to about 70% by weight of the composition. The particularly preferred polyol sugar is xylitol which is reported to have anti-cariogenic benefits. The use of xylitol in various products such as chewing gums is reported in U.S. Pat. No. 3,296,079 to Griffin, issued Jan. 3, 1967; U.S. Pat. No. 3,655,866, issued to Bilotti on Apr. 11, 1972; U.S. Pat. No. 3,914,434 issued to Bohni on Oct. 21, 1975; U.S. Pat. No. 4,000,320 issued to Klose, et al on Dec. 28, 1976 and U.S. Pat. No.

3,899,593 issued to Hammond, et al on Aug. 12, 1975, all of which are herein incorporated by reference.

A component which may be included in the present invention is an alkaline buffer which serves to raise or maintain the pH in the oral cavity. The term alkaline buffer is not meant to imply that the pH in the oral cavity must be within the alkaline range but rather that it is preferred that the pH of the oral cavity be in the alkaline range. In fact, the buffering capacity should be such that the pH of the oral cavity is maintained at from about 5.5 to about 10, most preferably from about 6 to about 9. Any alkaline buffer or combinations of alkaline buffers which provide the desired effect may be used. Prominently noted, is the use of bicarbonates particularly sodium bicarbonate to provide the desired pH effect. Other buffers which may be used include carbonates, sesquicarbonates, citrates, and polyphosphates including pyrophosphates, orthophosphates, tripolyphosphates, and hexametaphosphate.

The amount of buffer which is required will, of course, depend upon the acidic nature of the composition in which it is being used. It is generally found that employing the buffer at from about 1% to about 30% by weight of the composition ensures that the desired pH range in the oral cavity will be met. Preferably the amount of the alkaline buffer employed is from about 2% to about 20% by weight of the composition.

Another component which is desirably used in the present invention is a dental abrasive. Dental abrasives are particularly valuable in chewing gums due to the polishing action which occurs during mastication. The term dental abrasive includes all manner and form of such materials which are normally used in toothpaste, chewing gums, and the like. Specifically dicalcium diphosphate dihydrate is the preferred dental abrasive of the present invention. This particular material also serves to function as an alkaline buffer as described above. The use of dicalcium phosphate and its dihydrate powder are described in U.S. Pat. Nos. 3,011,949 and 3,655,866, issued respectively Dec. 5, 1961 and Apr. 11, 1972 to Bilotti, both of which are herein incorporated by reference.

Further dental abrasives which may be utilized in the present invention include calcium carbonate, sodium metaphosphate, aluminum hydroxide, magnesium carbonate, calcium sulphate, silicas including aerogels and xerogels, and tricalcium phosphate. Expanded disclosures of dental abrasives suitable for use in the present invention are found in U.S. Pat. No. 2,744,049, issued May 1, 1956 to Salzmann, et al, herein incorporated by reference. The amount of the dental abrasive employed in the present invention is generally within the range of from about 1% to 30%, preferably from about 1.5% to about 20% by weight.

Yet another desirable ingredient in the composition of the present invention is the use of glycerine. In the chewing gum aspect of the present invention glycerine serves to soften and maintain the chewability of the chewing gum for prolonged periods. The glycerine also adds to the sweetness of the composition. The glycerine is ordinarily added at levels of from about 0.01% to about 10%, preferably at from about 0.2% to about 5% by weight of the composition.

Where the term salt is employed in the present invention the cation may be any material which is accepted as safe for food or chewing gum uses. Preferably the cations are selected from a group consisting of sodium, potassium, calcium, magnesium, ammonium, and substituted ammonium and mixtures thereof. The sodium salt is most preferred in the present invention both from a cost and a solubility standpoint followed by the calcium and magnesium salts. Where additional germicidal effect is desired the ammonium or substituted ammonium salts are particularly valuable.

In vitro testing to determine the effectiveness of the compositions of the present invention is conducted in accordance with the accepted practices of determining plaque formation. For some of the general aspects of in vitro testing not discussed below, see "An In Vitro Method for Assessing the Plaque Forming Ability of Oral Bacteria," authored by McCabe et al reported in the ARCHIVES OF ORAL BIOLOGY, Volume 12, pages 1653–1656, 1967; and Effect of Microbial Interactions on In Vitro Plaque Formation by Streptococcus Mutans, by Miller et al reported in the JOURNAL OF DENTAL RESEARCH, March-April 1974, Volume 53, No. 2, pages 427–434, both of which are herein incorporated by reference.

The streptococcus mutans used in the experiment was strain 6715, in a three percent (3%) trypticase-soy broth, plus five percent (5%) sucrose. The streptococcus mutans was innoculated into ten (10) milliliters of sterile broth in a 20×150 mm test tube. Sterile twenty (20) gauge nichrome steel wires, 150 mm long and mounted in No. 2 rubber stoppers, were suspended in the media and incubated for twenty-four (24) hours at 37 degrees Celsius. For five (5) consecutive days, the wires were transferred into freshly reinoculated tubes of sterile media. They were then transferred through uninnoculated media for five (5) more days. In each instance, the wires protruded 37–38 mm below the surface of the medium. At the end of the ten (10) day period, the portion of the wire containing the bacterial (plaque) deposit is cut off and placed in a preweighed aluminum pan and dried to a constant weight at 70 degrees Celsius. The dry weight of the plaque is then established by burning off the plaque deposit in an open flame and reweighing the clean, dry wire. Blank samples of the wire were found not to lose any weight due to the open flame treatment.

To determine the extent of plaque growth in the presence of the compositions of the present invention, the foregoing procedure was followed with the exception of the introduction of the various components of the invention at stated levels. Inactive components, such as gum base, were not included in each test conducted, due to the difficulty in handling the test medium solutions. That is, where gum base is present in the test tube, it is difficult to avoid having some of the gum base adhere to the nichrome wire, thus giving false readings in the determination of the plaque. The gum bases and other inactive components of the present invention were, however, separately determined to have minimal effect on plaque growth.

In vivo testing is conducted with human volunteers, using a fully constituted product, containing the active plaque inhibiting portion of the composition and the inert ingredients. In particular, for the testing of the chewing gums, a group of twenty (20) volunteers is divided in random fashion into two (2) groups of ten (10) each. During the first week, one group will chew a controlled gum which is available on the market, while the second group uses a gum in accordance with the present invention. In the second week, regular oral hygiene will be followed by all subjects in the test. This is to ensure that all volunteers who are known to readily form plaque will not develop gingivitis or any other oral condition, which would affect their health or the test scores. During the third week, the groups are switched, such that the group which previously used the controlled gum will now use the gum made in accordance with the present invention and vice versa.

To demonstrate the effectiveness of the present invention, only a limited amount of chewing gum and chewing time by the subjects is allowed. Further, to demonstrate the effectiveness of the compositions of the present invention, the testing is conducted such that the subjects only chew the gum on one side of the mouth during the entire test. During the test period, the volunteers chew their assigned gum, once in the morning and once in the late afternoon for ten (10) minutes on the right side of the mouth only, under supervision, to ensure that the instructions are followed fully. An additional stick of gum is given to each volunteer to chew for ten (10) minutes before going to bed. This test is also conducted such that the gum is chewed only on the right side of the mouth. On the last day of the test period, intra-oral photographic records of the unstained anterior area of the mouth are made. Any gingivitis and dental plaque will be estimated and recorded, according to accepted scientific principles.

To further ensure that the compositions of the present invention are effective even in the absence of mastication, that is, a high degree of chewing which alone is known to have some cleaning benefits to the teeth, additional in vitro testing is conducted. In this test, freshly extracted human teeth were treated three (3) times daily with a fresh human saliva solution. The teeth received three (3) ten minute treatments at zero, three and six hour intervals each day, followed by incubation overnight. The tests were variously conducted for one or two days to determine the initial buildup of plaque in the control and test solutions. As described earlier the compositions of the present invention omitted inert ingredients which were not essential. The amount of plaque buildup on the teeth is determined by the difference in the optical density of the freshly extracted teeth and the teeth following the period of treatment in the saliva with and without the compositions of the invention present. In general, as noted in the examples, the foregoing series of three (3) tests, indicates a high degree of effectiveness of the compositions of the present invention over the control.

EXAMPLE I

A plaque inhibiting gum is prepared according to the present invention by mixing the following components and pressing the mixture into 3 gram sticks:

gum base—Paloja L. A. Dreyfus: 25%
xylitol: 10%
sodium bicarbonate: 2%
sorbitol: 35%
Sorbo (70% sorbitol in $H_2O$): 15%
dicalcium phosphate dihydrate: 5%
mannitol: 5%
glycerine: 0.5%
sodium lauryl sulfate: 0.8%
zinc oxide: 0.8%
balance dyes and coloring: q.s.

The chewing gum when tested as previously described is found effective in removing plaque from the surface of the teeth and in inhibiting the growth of new plaque.

In use it is suggested that the chewing gum be masticated as single sticks at least twice a day for a period of ten minutes each time for maximum effectiveness.

EXAMPLE II

A plaque inhibiting gum is prepared according to the present invention by mixing the following components and pressing the mixture into 3 gram sticks:

gum base—Paloja L. A. Dreyfus: 25%
xylitol: 10%
sodium bicarbonate: 2%
sorbitol: 35%
Sorbo (70% sorbitol in $H_2O$): 15%
dicalcium phosphate dihydrate: 5%
mannitol: 5%
glycerine: 0.5%
cinnamin oil: 0.8%
sodium lauryl sulfate: 0.8%
balance coloring: q.s.

The chewing gum when tested as previously described is found effective in removing plaque from the surface of the teeth and in inhibiting the growth of new plaque. The foregoing example may be modified by substituting peppermint or spearmint flavor with similar results.

In use it is suggested that the chewing gum be masticated as single sticks at least twice a day for a period of ten minutes each time for maximum effectiveness.

EXAMPLE III

A plaque inhibiting gum is prepared according to the present invention by mixing the following components and pressing the mixture into 3 gram sticks:

gum base—Paloja L. A. Dreyfus: 25%
xylitol: 10%
sodium bicarbonate: 2%
sorbitol: 35%
Sorbo (70% sorbitol in $H_2O$): 15%
dicalcium phosphate dihydrate: 5%
mannitol: 5%
glycerine: 0.5%
cinnamon oil: 0.8%
sodium lauryl sulfate: 0.8%
zinc oxide: 0.8%
balance coloring: q.s.

The chewing gum when tested as previously described is found effective in removing plaque from the surface of the teeth and in inhibiting the growth of new plaque. The foregoing example may be modified by substituting peppermint or spearmint flavor with similar results.

In use it is suggested that the chewing gum be masticated as single sticks at least twice a day for a period of ten minutes each time for maximum effectiveness.

EXAMPLE IV

Plaque inhibiting mints in hard form weighing 5 grams are prepared containing the following ingredients:

xylitol: 10%
sodium bicarbonate: 2% sorbitol: 65%
Sorbo (70% sorbitol in H₂O): 15%
mannitol: 5%
glycerine: 0.5%
cinnamon oil: 0.8%
sodium lauryl sulfate: 0.8%
zinc oxide: 0.8%
balance flavor and coloring: q.s.

The plaque inhibiting mint when used as previously described is found to be effective in inhibiting plaque formation on the surface of the teeth. The mint form of the present invention is preferably used after each meal by sucking on the mint for a period of five minutes.

Alternatively, substantially similar results are obtained by replacing the zinc oxide with an equivalent weight of the cinnamon oil. Further, an effective plaque inhibiting mint is formed as above but by omitting the cinnamon oil.

What is claimed is:

1. A chewing gum containing:
 (a) from about 10% to about 95% by weight of a gum base; and,
 (b) from about 0.001% to about 20% by weight of a mixture of an alkyl sulfate salt and a zinc compound in a weight ratio of from about 1,000:1 to about 1:1,000.

2. The chewing gum of claim 1 having from about 0.001% to 15% of the alkyl sulfate salt and from about 0.001% to 5% of the zinc compound.

3. The chewing gum of claim 2 having from about 0.005% to 5% of the alkyl sulfate salt and from about 0.005% to 3% of the zinc compound.

4. The chewing gum of claim 3 having from about 0.1% to 3% of the alkyl sulfate salt and from about 0.01% to 2% of the zinc compound.

5. The chewing gum of claim 4 wherein the cation of the salt is selected from the group consisting of sodium, potassium, calcium, magnesium, ammonium, and substituted ammonium and mixtures thereof.

6. The chewing gum of claim 5 wherein the zinc compound is selected from the group consisting of zinc phosphates, zinc sulfates, zinc chlorides, zinc fluorides, zinc oxides and zinc fatty acids.

7. The chewing gum of claim 5 wherein the zinc compound is selected from the group consisting of zinc phenolsulfonate, zinc oxide and the stearic acid salt of zinc.

8. The chewing gum of claim 7 containing from about 5% to about 80% by weight of a member selected from the group consisting of xylitol, sorbitol, and mannitol and mixtures thereof.

9. The chewing gum of claim 8 containing from about 0.01% to about 10% by weight of glycerine.

10. The chewing gum of claim 9 containing from about 1% to about 30% by weight of a member selected from the group consisting of alkaline buffers and dental abrasives and mixtures thereof.

11. The chewing gum of claim 10 containing a plaque inhibiting flavor at from about 0.05% to 10% by weight.

12. The chewing gum of claim 11 wherein the zinc compound is selected from the group consisting of zinc oxide and zinc stearate and mixtures thereof.

13. The chewing gum of claim 12 wherein the alkyl sulfate salt is lauryl sulfate.

* * * * *